(12) United States Patent
Subhash et al.

(10) Patent No.: US 6,343,502 B1
(45) Date of Patent: *Feb. 5, 2002

(54) APPARATUS AND METHOD FOR DETERMINING THE DYNAMIC INDENTATION HARDNESS OF MATERIALS

(75) Inventors: Ghatu Subhash; Abhijit Chandra; Brian J. Koeppel, all of Houghton, MI (US)

(73) Assignee: Michigan Technological University, Houghton, MI (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/128,352

(22) Filed: Aug. 3, 1998

Related U.S. Application Data (63) Continuation of application No. 08/732,644, filed on Oct. 7, 1996, now abandoned.

(51) Int. Cl.⁷ ................................................ G01N 3/48
(52) U.S. Cl. ........................................................ 73/81
(58) Field of Search .................... 73/78, 81, 82, 73/84, 85, 12.01, 12.04, 12.06, 12.09, 12.13

(56) References Cited

U.S. PATENT DOCUMENTS

| | | | | |
|---|---|---|---|---|
| 3,956,925 A | * | 5/1976 | Smith | 73/81 |
| 3,999,424 A | | 12/1976 | Pellissier | 73/81 |
| 4,019,376 A | | 4/1977 | Iwasaki | 73/81 |
| 4,116,041 A | * | 9/1978 | Tholén et al. | 73/84 |
| 5,313,825 A | | 5/1994 | Webster et al. | 73/84 |
| 5,576,483 A | * | 11/1996 | Bonin | 73/105 |
| 5,616,833 A | | 4/1997 | Anderson | 73/84 |
| 5,804,707 A | * | 9/1998 | Scarton et al. | 73/82 |

FOREIGN PATENT DOCUMENTS

| | | | |
|---|---|---|---|
| RU | 226917 | 8/1967 | 73/84 |
| RU | 751903 | 7/1980 | 73/84 |
| RU | 1344860 | 10/1987 | 73/82 |
| RU | 1344861 | 10/1987 | 73/82 |
| RU | 1375994 | 2/1988 | 73/82 |

OTHER PUBLICATIONS

Product Brochure, New Age Industries, "Portable Rockwell Hardness Testing System".

Product Brochure, New Age Industries, "Pin Brinell Portable Hardness Testing System", Technical Bulletin #10.

Worldwide Web Page (www.corvib.on.ca/index.html) entitled "Equotip Hardness Tester".

American Society for Testing and Materials, Standard Test Method for E92–82 (1992) el VICKERS Hardness of Metallic Materials, 1996.

American Society for Testing and Materials, A956–96 Standard Test Method for Equotip Hardness Testing of Steel Products, 1996.

* cited by examiner

Primary Examiner—Hezron Williams
Assistant Examiner—Nashmiya Fayyaz
(74) Attorney, Agent, or Firm—Michael Best & Friedrich LLP (57) ABSTRACT

An apparatus and method for determining dynamic indentation hardness values of a material using a propagating stress wave to make an indentation in the material. The invention provides such values without any prior knowledge of the material properties and enables the dynamic indentation hardness values to be directly compared to static indentation hardness values for the material.

28 Claims, 12 Drawing Sheets

APPARATUS AND METHOD FOR DETERMINING THE DYNAMIC INDENTATION HARDNESS OF MATERIALS

RELATED APPLICATIONS

This application is a continuation of U.S. patent application Ser. No. 08/732,644 filed Oct. 7, 1998, now abandoned.

FIELD OF THE INVENTION

The invention relates to an apparatus and method for determining the indentation hardness of a material, and more particularly, to an apparatus and method for determining the dynamic indentation hardness of a material.

BACKGROUND OF THE INVENTION

Indentation hardness measurements have been used for several decades by machinists and researchers in various fields. Indentation hardness is a measure of a material's resistance to penetration or permanent deformation. Indentation hardness measurements have been used to successfully monitor the effectiveness of processes such as heat treating, casting, forming, and welding. For the machinist, indentation hardness may indicate a material's resistance to cutting.

Indentation hardness measurements are typically obtained by subjecting a material to a static indentation force with an indentor for typically 10–15 seconds, measuring the area of the indentation and then calculating the static indentation hardness using a test standard such as, for example, ASTM Test Method E92-82 for Vickers indenters which is set forth below:

Vickers Hardness $(HV)=2P\sin(\alpha/2)/d^2=1.8544P/d^2$ wherein p=load (kgf)
d=mean indentation diagonal (mm)
α=face angle of diamond=136 degrees.

Although traditional static indentation hardness measurements provide insight into a material's behavior during a specific process, these measurements do not accurately and sufficiently represent a material's response during a dynamic event such as metal cutting or material removal during high speed machining. This is because deformation mechanisms of most materials are known to be rate dependent. For example, increased yield and flow stresses at higher strain rates in the case of metals, and increased fracture stress in the case of ceramics are rate dependent effects. Therefore, static indentation measurements do not completely represent a material's behavior under dynamic events.

Many engineering applications involve dynamic loading conditions, e.g., machining, crashworthiness of automotive structures, impacts of space debris on space structures, and penetration resistance of armor materials. Existing hardness testers either measure only static indentation hardness or use a rebound technique to measure dynamic indentation hardness. The rebound technique to measure dynamic indentation hardness assumes constant yield pressure, neglects thermal effects and neglects sensitivity to indenter velocity therefore making the measurement of dynamic indentation hardness indirect and inaccurate. Moreover, the dynamic indentation hardness determined by the rebound technique cannot be compared to existing static indentation hardness values.

Accordingly, there is a need for an apparatus and method that can measure indentation hardness at strain rates similar to those encountered in actual dynamic processes. With the increasing use of composites in every realm of technology, there is a demand for quick and accurate determination of effective properties of these new materials. Dynamic indentation hardness measurements plays a key role in these activities.

SUMMARY OF THE INVENTION

The invention provides an apparatus and method for determining the dynamic indentation hardness of a material. The invention requires no prior knowledge of material characteristics which simplifies the measurement of dynamic indentation hardness. The apparatus and method utilizes a propagating stress wave to make a single indentation in the material. By suitably positioning a load transducer, the dynamic indentation hardness of a material can be determined accurately. The apparatus and method is useful in evaluating dynamic material response under high rate loading processes such as material removal during machining, dynamic wear, impact loading, and dynamic fragmentation. The present invention is of significant value in assessing a material's ability to resist a specified dynamic load. Further, the invention can be used as a tool to quickly screen potential new materials to assess their suitability for dynamic applications. The obtained dynamic hardness can be directly compared to its static counterpart.

The invention provides for an apparatus and method for determining dynamic indentation hardness of a material using a propagating stress wave in a long slender bar. By mounting an indenter at one end and introducing a stress wave of suitable amplitude and duration at the other end, the invention delivers a single compressive stress pulse of required characteristics into the specimen material.

It is an object of the present invention to provide an improved apparatus and method for determining the indentation hardness of a material.

It is another object of the present invention to provide an apparatus and method for determining the dynamic indentation hardness of a material.

It is another object of the present invention to provide an apparatus and method for determining the dynamic indentation hardness of a material using loading pulses of less than one second.

It is another object of the present invention to provide an apparatus and method for determining indentation hardness having the load cell on the incident bar.

Other features and advantages of the invention will become apparent to those of ordinary skill in the art upon review of the following detailed description, claims, and drawings.

Before one embodiment of the invention is explained in detail, it is to be understood that the invention is not limited in its application to the details of construction and the arrangement of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

DETAILED DESCRIPTION OF THE PREFERRED EMBODIMENT

Figure 1:
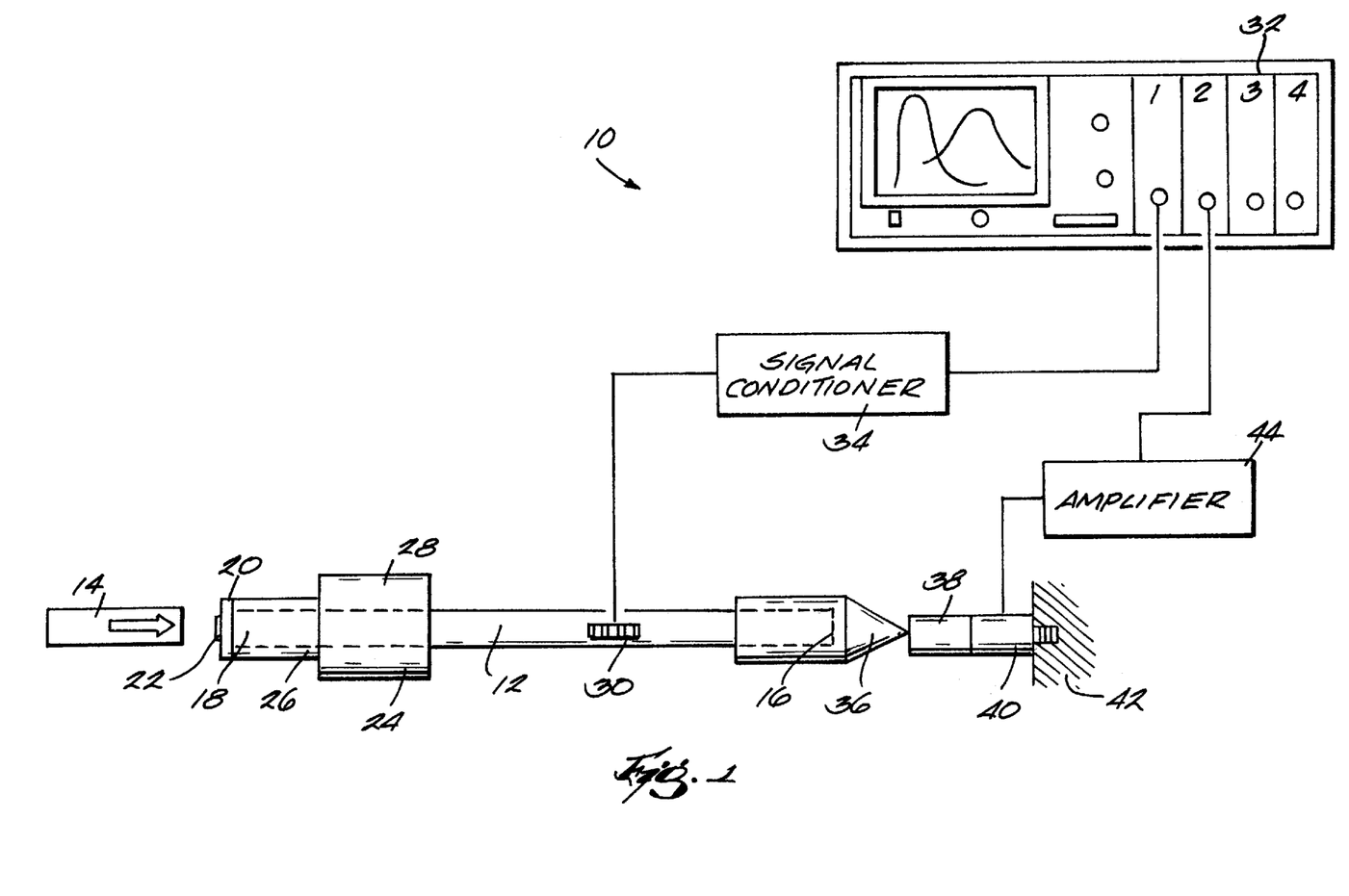
FIG. 1 is a side view of a first embodiment of the invention.

Referring now to FIG. 1, there is shown an apparatus 10 for measuring the dynamic indentation hardness of a material. Materials to be measured may include, for example, metals, ceramics, plastics and composites. The apparatus 10 includes a long slender incident bar 12 and a striker bar 14 both preferably fabricated of maraging steel. Preferably, the incident bar 12 is a modified Hopkinson pressure bar having a first end 16, a second end 18 and a flange 20 adjacent end 18. Optionally, the second end 18 can include a pulse shaper 22 that is mounted on flange 20 and is preferably copper. It should be noted however that a pulse shaper is not required for operation of the apparatus 10. The striker bar 14 is launched such as from a gas gun at a predetermined velocity toward the incident bar 12. The impact at the end 18 of the incident bar 12 generates a compressive stress pulse in the incident bar 12 which travels toward the end 16. The amplitude of the stress pulse depends upon the velocity of the striker bar 14. Stress pulse durations of 50–200 $\mu$s can be achieved by varying the length of the striker bar 14.

Preferably, the end 18 of the incident bar 12 is modified with a momentum trap 24 which includes a collar 26, or incident tube, surrounding the incident bar 12 and a reaction mass 28 on the incident bar 12. The collar is positioned between flange 20 and the reaction mass. The momentum trap 24 is adapted to the configuration of the incident bar 12 and functions as described in Nemat-Nasser et al., Proc. R. Soc. Lond. A 435:371–391 (1991) which is incorporated herein by reference. More particularly and in operation, when the striker bar impacts the flange 20 at a given velocity it imparts a common axial strain to the collar 26 (incident tube) and the incident bar 16. The compression pulse in the incident bar travels along this bar toward the specimen 38. The compression pulse in the collar reflects from the reaction mass as compression, and reaches the transfer flange at the same instant that the tension release pulse which is reflected from the free end of the striker, reaches the end in contact with the transfer flange. The striker bar begins to bounce back, away from the transfer flange, as the transfer flange is loaded by the compression pulse traveling along the collar. This compression pulse then imparts a tensile pulse to the incident bar. It is instructive to note and with reference to the structure in FIG. 1, that when the incident tube in contact with the transfer flange at its one end, is free at the other end, then it serves as a "momentum trap" for tensile pulses moving in the incident bar toward the transfer flange. The tensile pulse reflects off the free end of the transfer flange as compression. This compressive pulse is then fully transferred into the incident tube in contact with the flange, when the impedances are matched. The compression then reflects off the free end of the tube as tension, and is trapped in the tube which begins to move away from the transfer flange once the reflected tension reaches the tube's end in contact with the flange. Hence, once the sample is loaded in compression by the initial compressive segment of the stress pulse, it will remain intact to be recovered, since all subsequent pulses which move toward the specimen are then tensile. Therefore, the initial strike impacts a compression pulse followed by a tension pulse and as described above all subsequent resulting pulses will be in tension relative to the indenter 36. Accordingly, only a single compression stress pulse, the first stress pulse, reaches the end 16 of the incident bar 12. Through use of the pulse shaper 22 on the end 18 of the incident bar 12, loading and unloading rates can be customized.

Optionally, a strain gage 30 can be mounted on the incident bar 12 to confirm constant loading rates over a desired time duration. The strain gage 30 can be of various types such as, for example, model WK-06-250BF10C manufactured by M&M of Raleigh, North Carolina. The strain gage 30 captures the complete history of the stress pulse which is then recorded on a high speed multi-channel digital oscilloscope 32. A signal conditioner 34, such as a wheatstone bridge, is positioned between the strain gage 30 and the oscilloscope 32.

An indenter 36 is mounted on the end 16 of the incident bar 12. Preferably, the indenter 36 is a diamond indenter of the Vickers type such as a Vickers diamond indentor available from Leco Corp. of St. Joseph, Michigan. However, it should be noted that other types of indenters can be used with the present invention such as ball or cone indenters. In the first embodiment as shown in FIG. 1, the specimen 38 of material to be tested is mounted to a load transducer such load cell 40. The load cell 40 is mounted to a stationary surface 42. Preferably, the load cell 40 is a high natural frequency load cell of, for example, 200 kHz such as model 9213 from Kistler of Amherst, N.Y.

Figure 2:
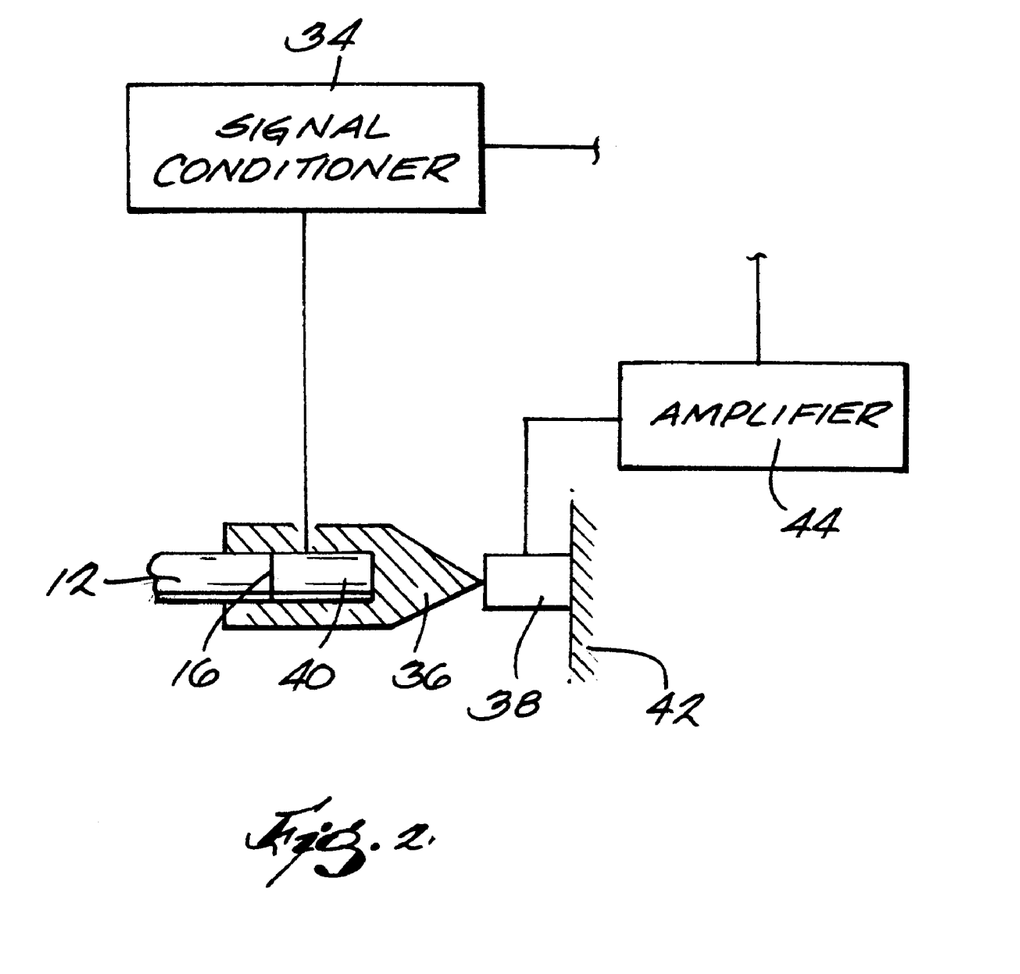
FIG. 2 is a partial side view of a second embodiment of the invention.
Figure 3A:
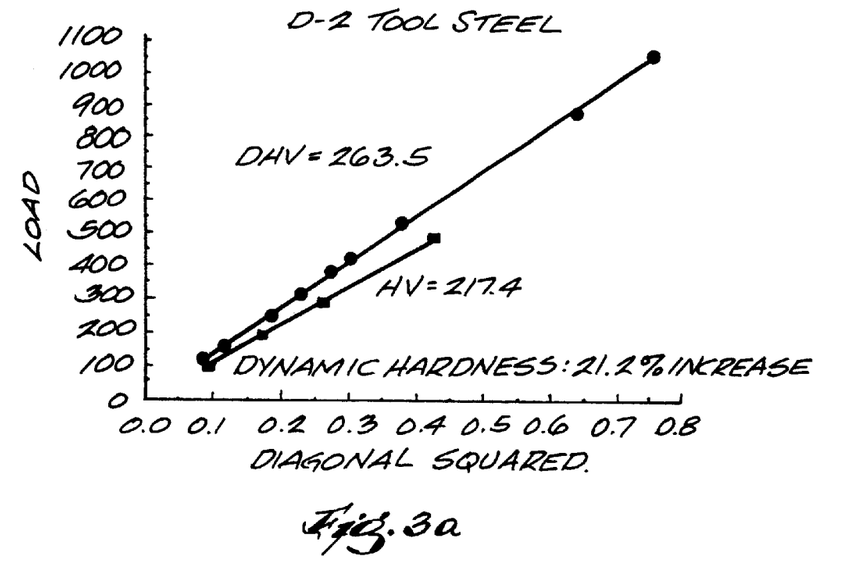
FIGS. 3(a)–(e) are charts of load in Newtons v. mean indentation diagonals in mm. squared for tool steels.
Figure 3B:
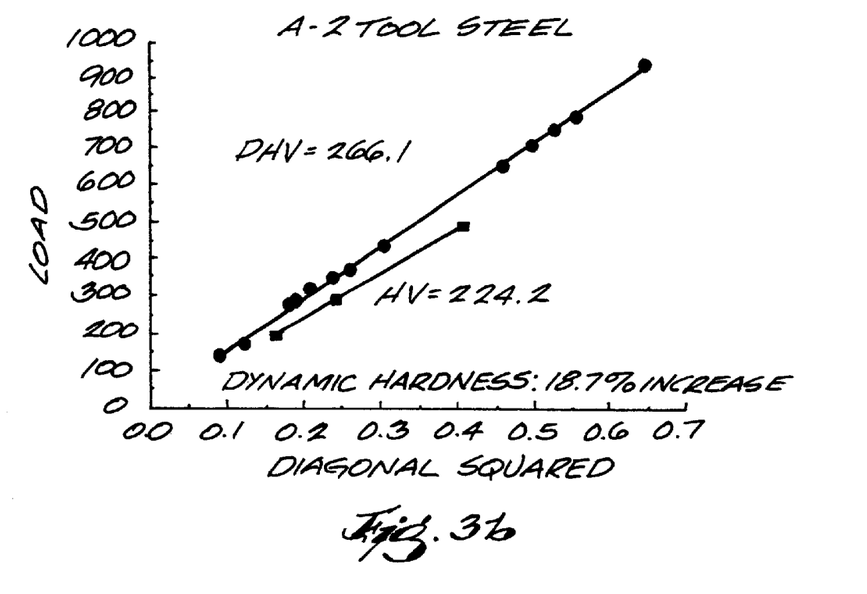
Figure 3C:
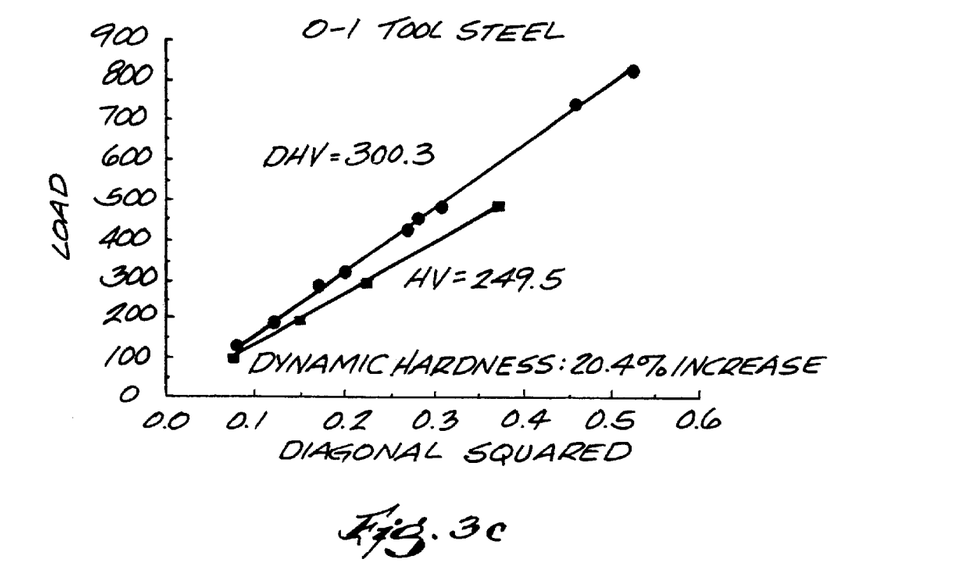
Figure 3D:
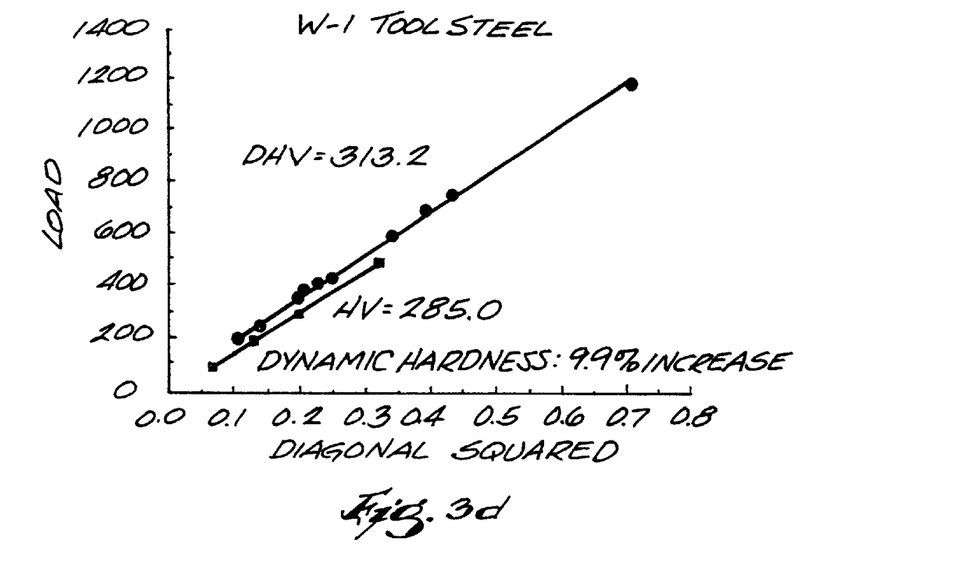
Figure 3E:
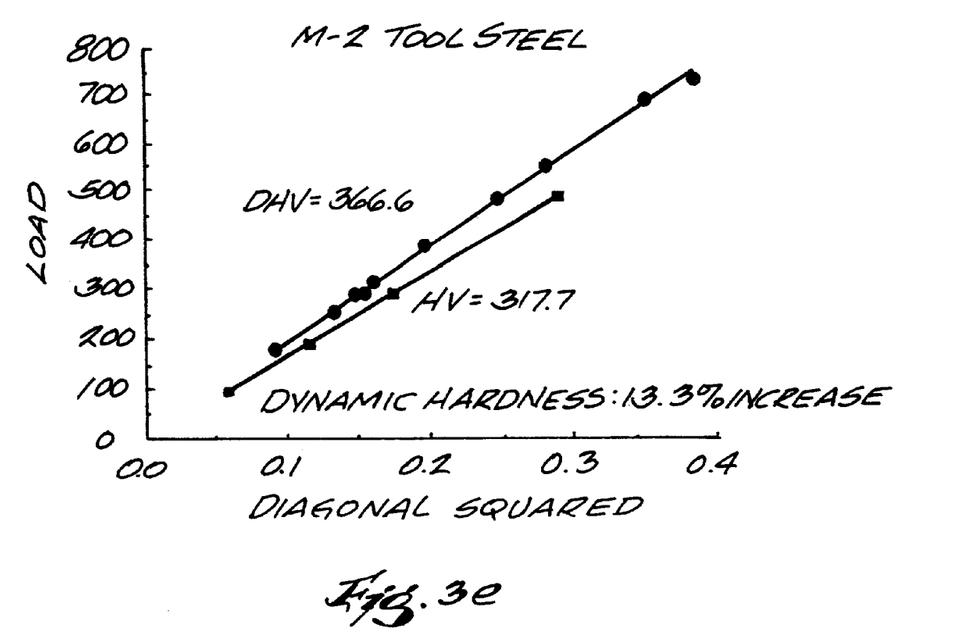
Figure 4A:
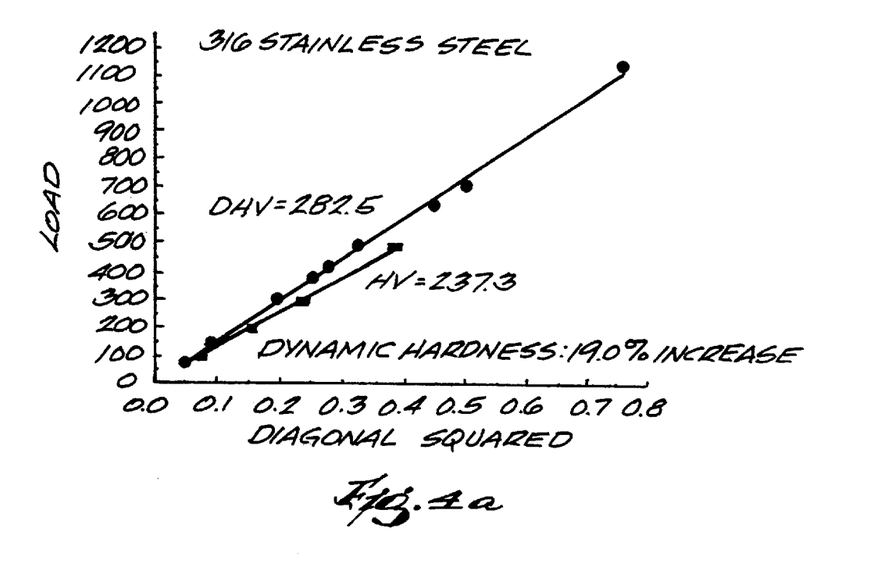
FIGS. 4(a)–(d) are charts of load in Newtons v. mean indentation diagonals in mm. squared for stainless steels.
Figure 4B:
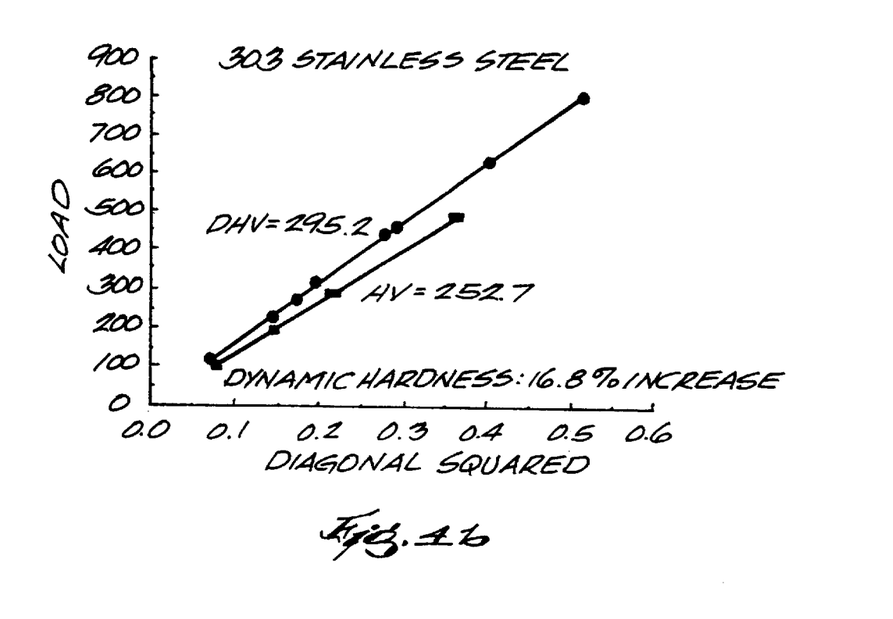
Figure 4C:
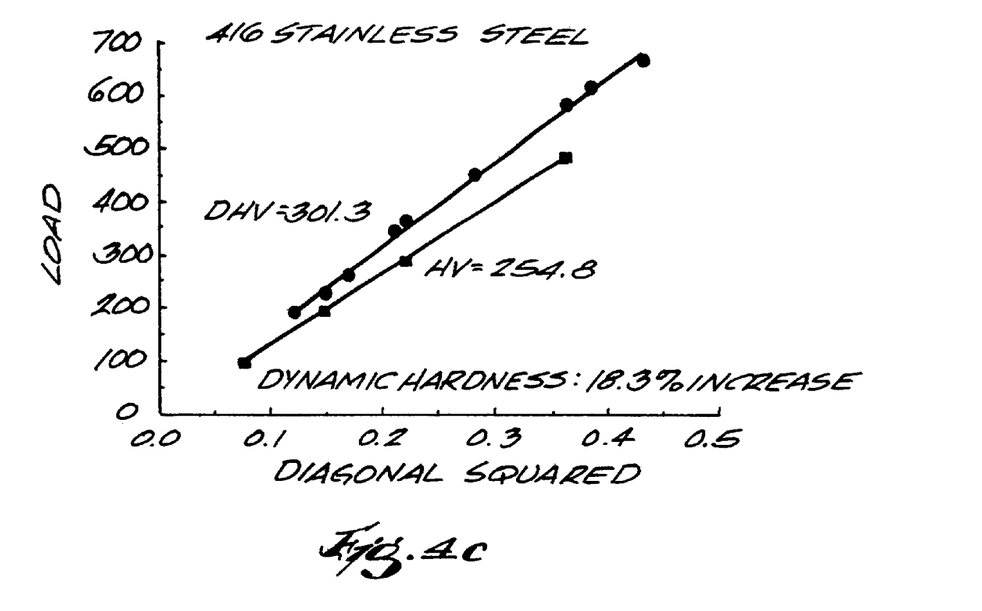
Figure 4D:
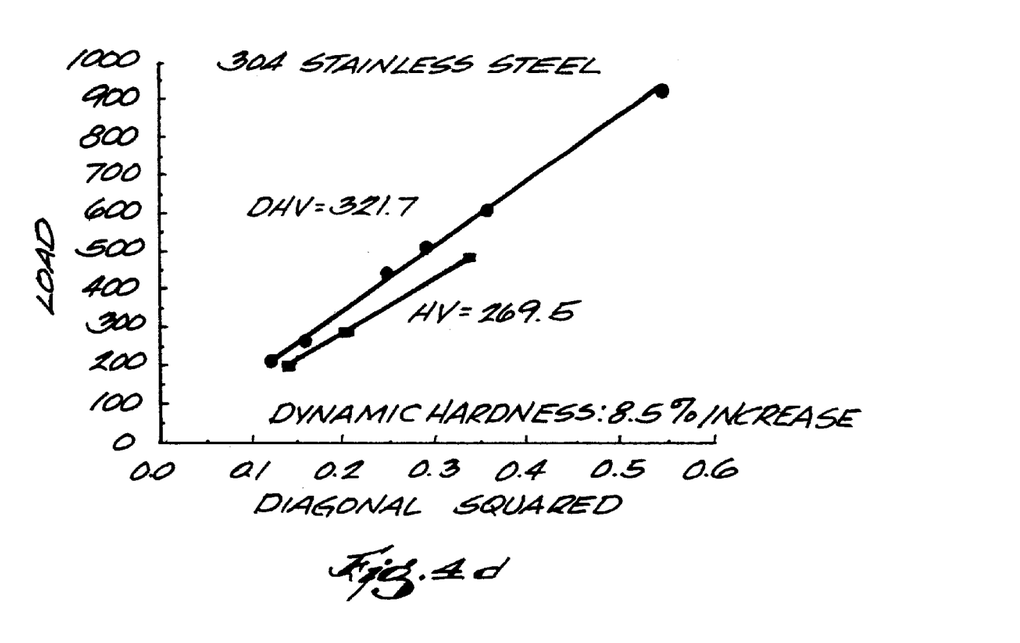
Figure 7:
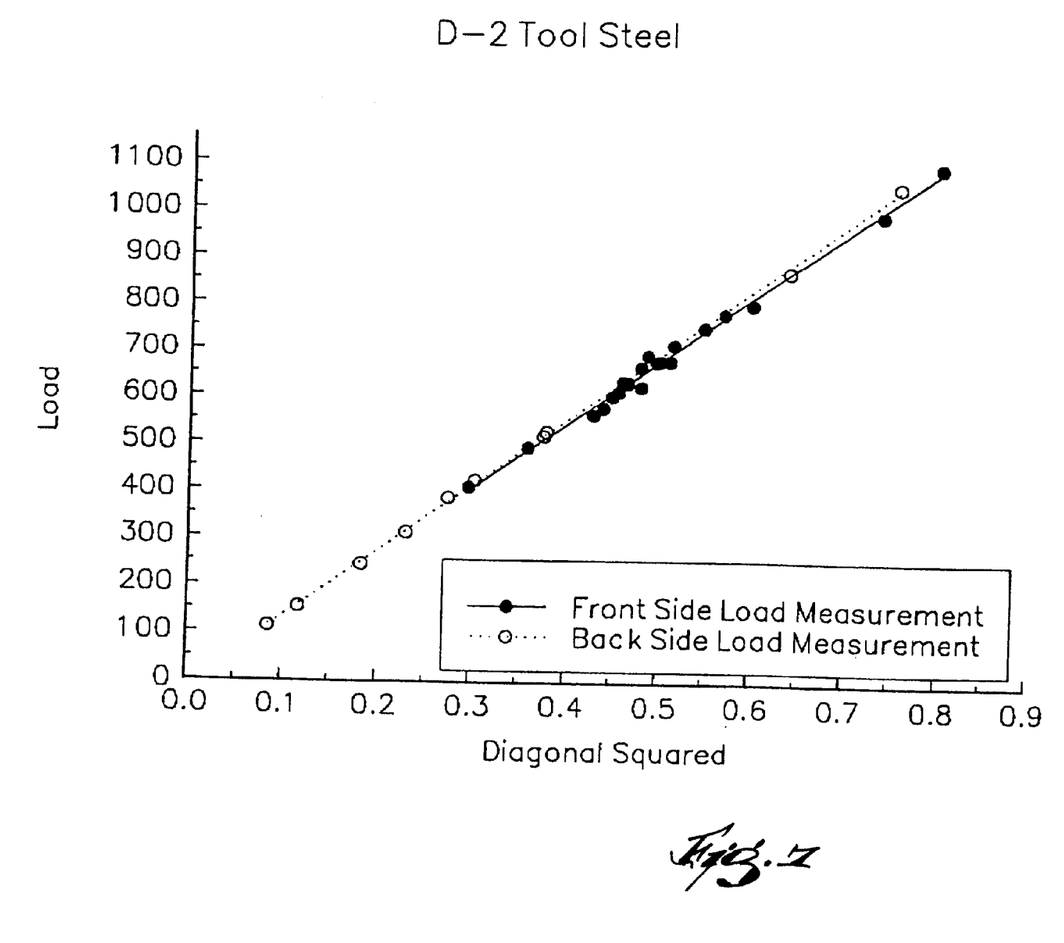
FIG. 7 is a chart of load in Newtons v. mean indentation diagonals in mm. squared for D-2 Tool Steel for both placements of a load cell, front and back.

In another embodiment as shown in FIG. 2, the load cell 40 can be positioned on the incident bar 12 adjacent the indenter 36. The positioning of the load cell 40 is often dependent upon space limitations where the apparatus 10 is to function. Although the positioning of the load cell 40 between the specimen 38 and the surface 42 yields a cleaner electronic signal, the indentation hardness results for a particular specimen 38 for both load cell positions are the same as demonstrated in FIG. 7 for D-2 Tool Steel.

The striker bar 14 impacting the incident bar 12 propagates a stress pulse along the incident bar 12 causes the indenter 36 to make a single indentation in the specimen 38. Upon indentation, the complete loading history of the specimen 38 is captured by load cell 40 in conjunction with an amplifier 44, such as a charge amplifier and recorded on the oscilloscope 32. The mean indentation diagonal of the specimen 38 is then determined either manually such as with the aid of a microscope or automatically measured such as with the aid of a laser measurement system.

With the load value from the recorded signal on the oscilloscope 32 and the mean indentation diagonal value, the dynamic hardness can be calculated manually or with the aid of a computer. For example, with the use of a Vickers indenter, the present invention conforms to the requirements of ASTM Test Method E92-82 for static Vickers hardness measurements and extends the concepts to the dynamic range. Accordingly, the dynamic indentation hardness value is calculated with the following formula:

$$\text{Dynamic Vickers Hardness (DHV)} = 2P\sin(\alpha/2)/d^2 = 1.8544 P/d^2$$

wherein
 p=load (kgf)
 d=mean indentation diagonal (mm)
 α=face angle of diamond=136 degrees.

It should be noted that with the use of other indenters, corresponding formulas, such as the ASTM Test Methods, are to be employed.

Optionally, a integrated circuit could be conventionally constructed and made part of a dynamic indentation hardness measurement device to automatically make the above calculation.

Figure 5A:
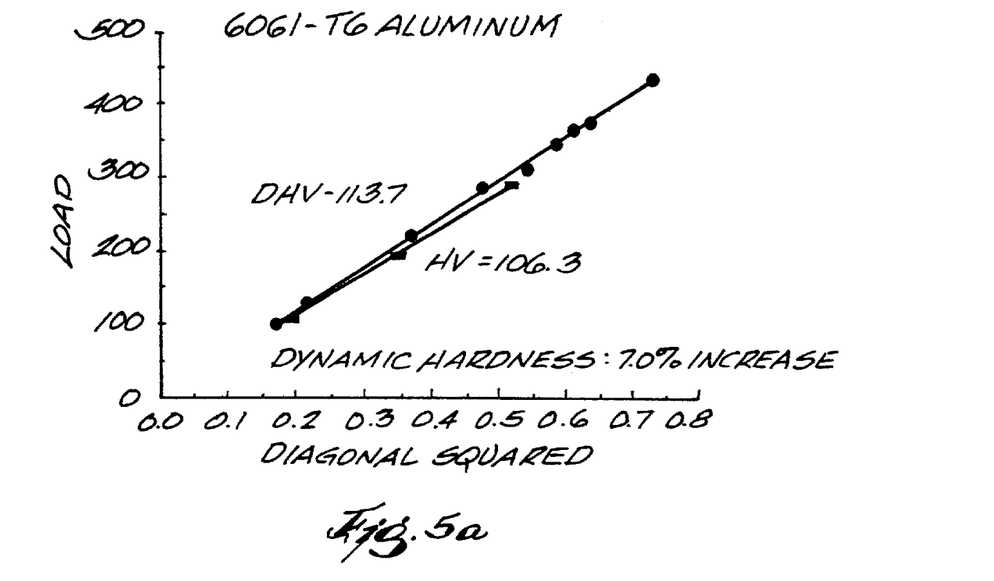
FIGS. 5(a)–(b) are charts of load in Newtons v. mean indentation diagonals in mm. squared for FCC materials.
Figure 5B:
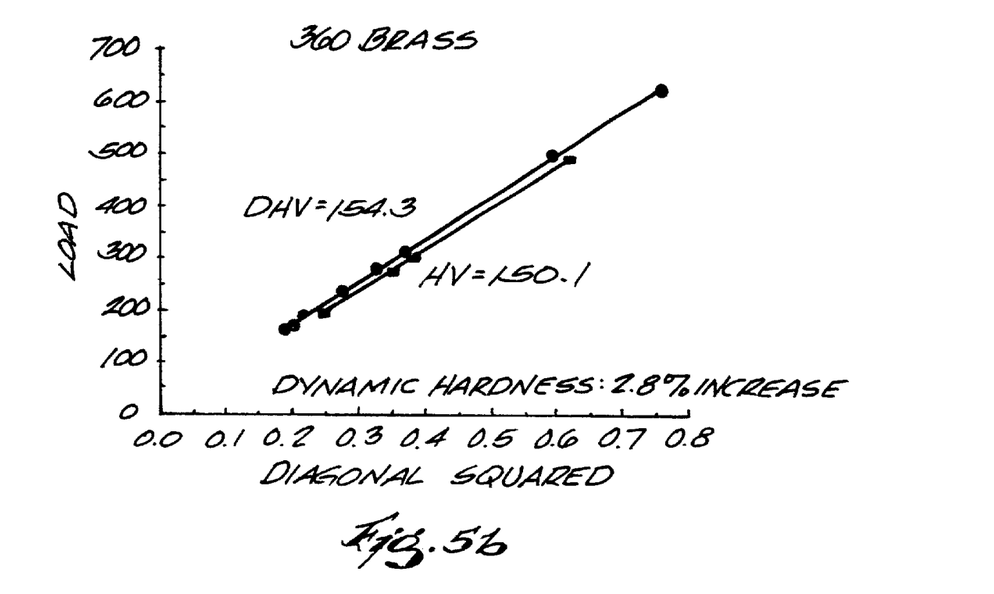
Figure 6A:
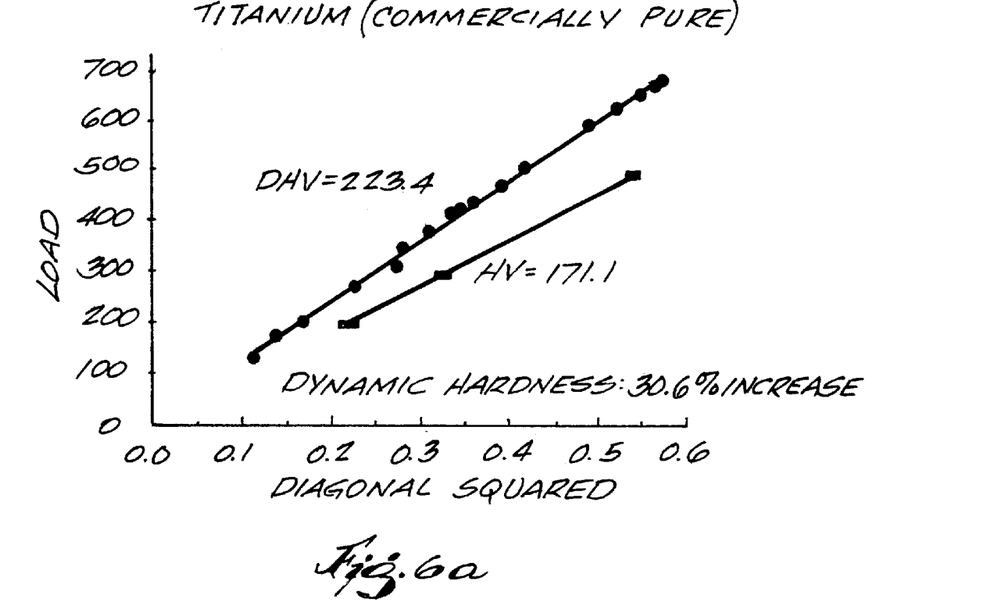
FIGS. 6(a)–(b) are charts of load in Newtons v. mean indentation diagonals in mm. squared for HCP materials.
Figure 6B:
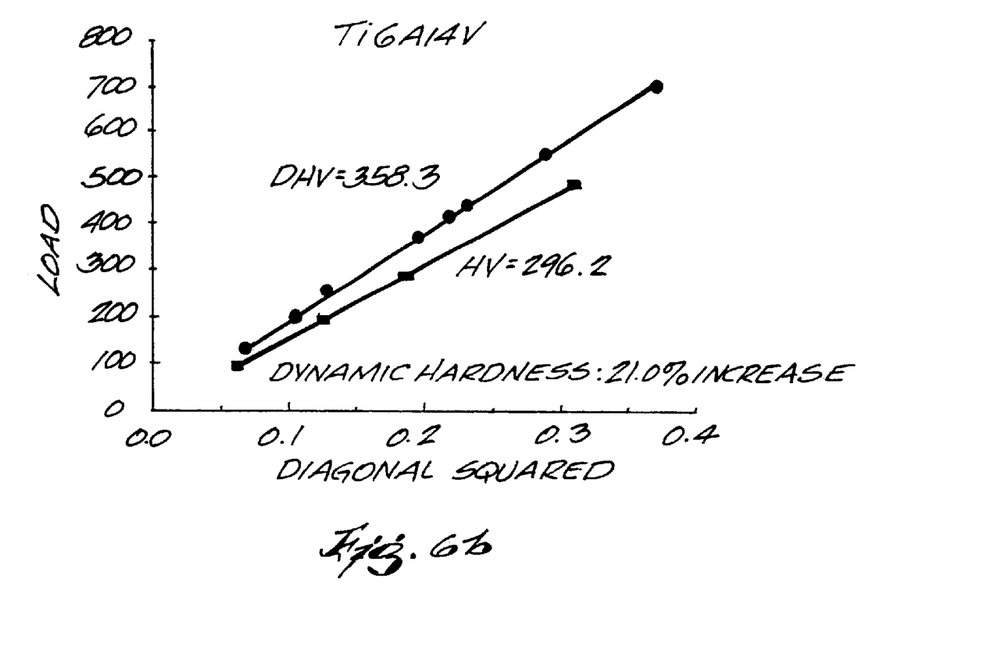
Figure 8:
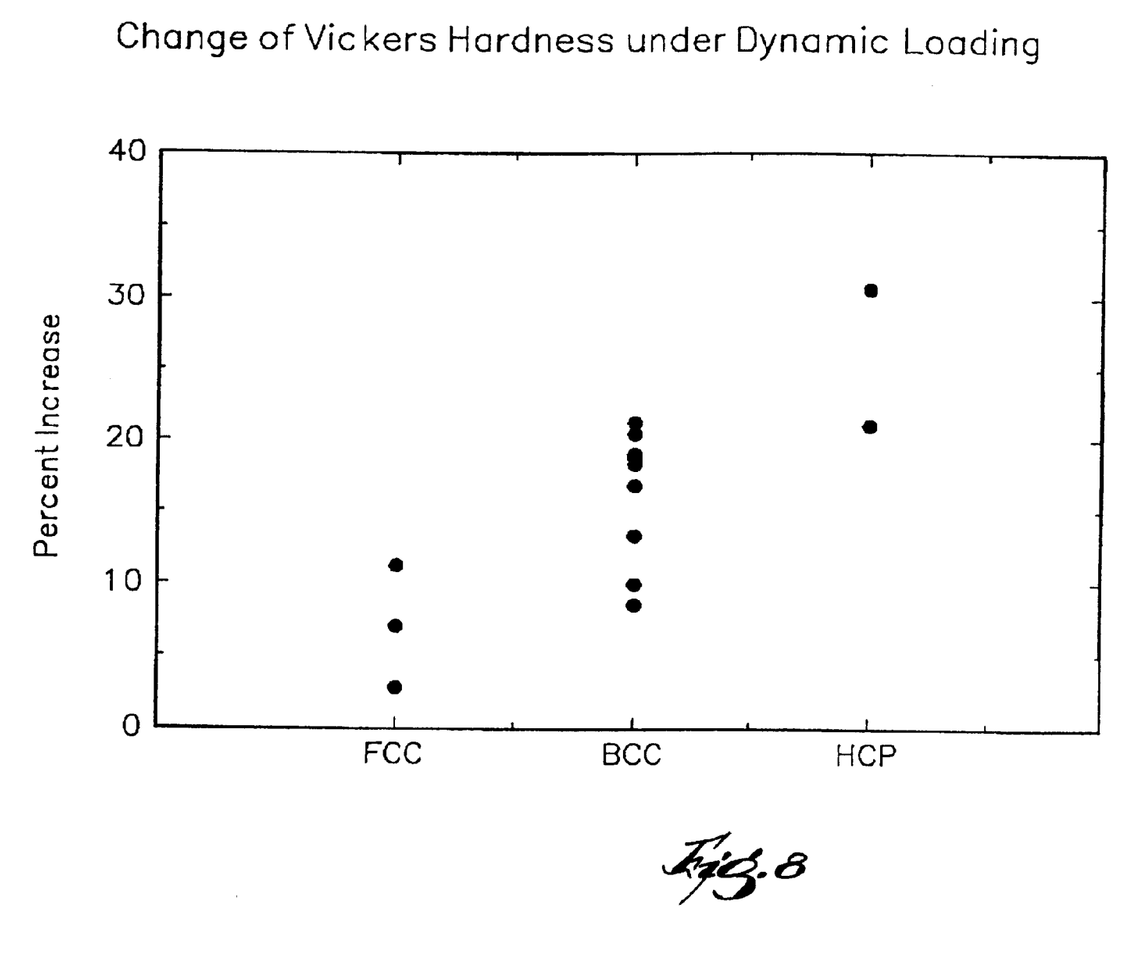
FIG. 8 is a chart entitled Change of Vickers Hardness under Dynamic Loading.
Figure 9:
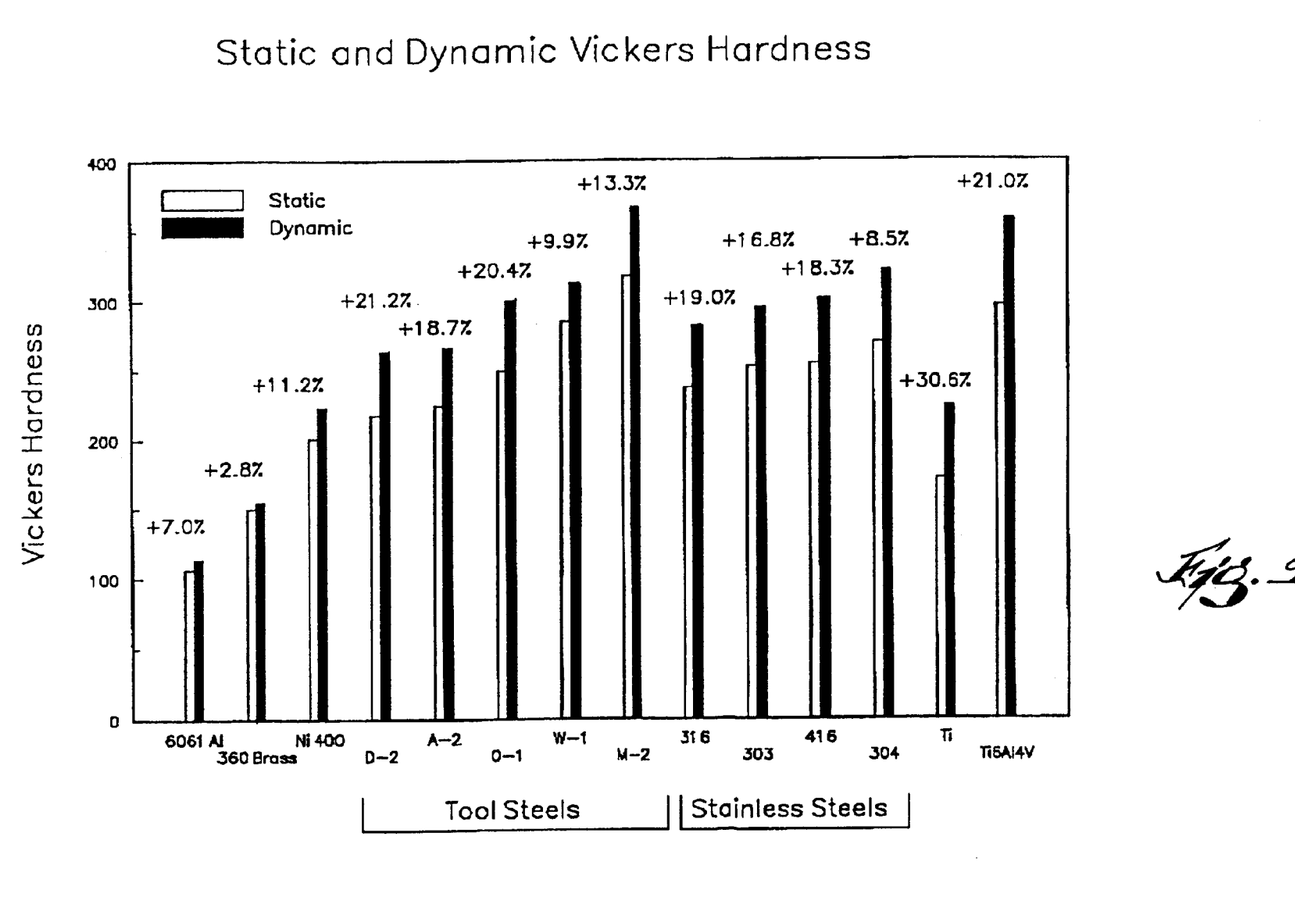
FIG. 9 is a chart entitled Static and Dynamic Vickers Hardness.

Using the apparatus 10 and method described above, the dynamic indentation values can be compared to the static indentation values of a particular material to determine the rate sensitive nature of the material. Static indentation hardness values can be obtained from conventional static indentation hardness testers such as model V-100-C2 available from Leco Corp. For some materials such as metals, dynamic indentation hardness can be up to 30% greater than the static indentation hardness. See for example FIGS. 3(a)–(e) pertaining to tool steels, FIGS. 4(a)–(d) pertaining to stainless steels, FIGS. 5(a)–(b) pertaining to FCC materials, FIGS. 6(a)–(b) pertaining to HCP materials and FIGS. 8 and 9.

The apparatus and method described above for measuring dynamic indentation hardness enables the following advantages.

Unlike present dynamic indentation testers, the present invention uses the same scale as conventional static indentation testers therefore making comparisons possible and accurate.

The present invention determines dynamic indentation hardness values many scales of magnitude quicker than the prior art wherein the loading period is typically 10–15 seconds. In contrast, the loading times for the present invention are on the order of 50–200 μs.

Unlike other dynamic indentation testers, the present invention does not require any prior knowledge of the material to be tested.

Unlike other dynamic indentation testers, the present invention calculates a dynamic indentation hardness values that is load independent, which is a requirement of a material property.

The present invention enables all of the above advantages while maintaining simplicity of use.

We claim:

1. An apparatus for determining the dynamic indentation hardness of a material, said apparatus comprising:
 an incident bar having a first, impact end;
 a striker bar that contacts said impact end of said incident bar and propagates a stress wave of a predetermined amplitude and duration along said incident bar;
 an indenter on said incident bar and spaced from said impact end, said indenter being adapted to contact the material;
 a load transducer positioned in contact with the material; and
 a momentum trapping means at said impact end of said incident bar for permitting only a single compression pulse to reach said indenter.

2. An apparatus for determining the dynamic indentation hardness of a material as set forth in claim 1 wherein said momentum trapping means is mounted on said first end and wherein said striker bar contacts said momentum trapping means.

3. An apparatus for determining the dynamic indentation hardness of a material as set forth in claim 1 wherein said indenter is mounted on a second end of said incident bar opposite said first end.

4. An apparatus for determining the dynamic indentation hardness of a material as set forth in claim 1 wherein said incident bar is a long slender rod.

5. An apparatus for determining the dynamic indentation hardness of a material as set forth in claim 1 wherein said load transducer is a load cell.

6. An apparatus for determining the dynamic indentation hardness of a material as set forth in claim 5 wherein said load cell is a high frequency load cell.

7. An apparatus for determining the dynamic indentation hardness of a material as set forth in claim 1 and further including an oscilloscope in communication with said load transducer.

8. An apparatus for determining the dynamic indentation hardness of a material as set forth in claim 1 and further including a computer in communication with said load transducer.

9. An apparatus for determining the dynamic indentation hardness of a material as set forth in claim 1 wherein said indenter is a Vickers type diamond indentor.

10. An apparatus for determining the dynamic indentation hardness of a material as set forth in claim 1 and further including a means for moving said striker bar into contact with said incident bar.

11. An apparatus for determining the dynamic indentation hardness of a material as set forth in claim 1 and further including an amplifier in communication with said load transducer.

12. An apparatus for determining the dynamic indentation hardness of a material, said apparatus comprising:
 an incident bar having a first, impact end and a second end;
 a striker bar that contacts said first, impact end of said incident bar and propagates a stress wave of a predetermined amplitude and duration along said incident bar;
 an indenter mounted on said incident bar and spaced from said impact end, said indenter having a tip that is adapted to contact the material;
 a load transducer positioned between said second end of said incident bar and said tip of said indenter; and
 a momentum trapping means at said impact end of said incident bar for permitting only a single compression pulse to reach said indenter.

13. An apparatus for determining the dynamic indentation hardness of a material as set forth in claim 12 and further including a means for moving said striker bar into contact with said incident bar.

14. An apparatus for determining the dynamic indentation hardness of a material as set forth in claim 12 wherein said incident bar is a long slender rod.

15. An apparatus for determining the dynamic indentation hardness of a material as set forth in claim 12 wherein said load transducer is a load cell.

16. An apparatus for determining the dynamic indentation hardness of a material as set forth in claim 12 and further including an amplifier in communication with said load transducer.

17. An apparatus for determining the dynamic indentation hardness of a material as set forth in claim 12 and further including an oscilloscope in communication with said load transducer.

18. An apparatus for determining the dynamic indentation hardness of a material as set forth in claim 12 and further including a computer in communication with said load transducer.

19. An apparatus for determining the dynamic indentation hardness of a material as set forth in claim 12 wherein said indenter is a Vickers type diamond indentor.

20. An apparatus for determining the dynamic indentation hardness of a material, said apparatus comprising:

an incident bar having an impact end;

a striker bar that contacts said impact end of said incident bar and propagates a stress wave along said incident bar;

a load transducer on said incident bar, an indenter mounted on said incident bar in spaced relation from said impact end and adapted to contact the material; and means at said impact end for permitting only a single compression pulse to reach said indenter.

21. The apparatus of claim 20 wherein said striker bar contacts said means for permitting only a single compression pulse.

22. The apparatus of claim 20 wherein said indenter is mounted on a second end of said incident bar opposite said impact end.

23. The apparatus of claim 20 wherein said load transducer is positioned in contact with the material.

24. The apparatus of claim 20 wherein said load transducer is high frequency load cell.

25. The apparatus of claim 20 and further including an oscilloscope in communication with said load transducer.

26. The apparatus of claim 20 and further including a computer in communication with said load transducer.

27. The apparatus of claim 20 wherein said indenter is a Vickers type diamond indentor.

28. The apparatus of claim 20 and further including an amplifier in communication with said load transducer.

* * * * *

UNITED STATES PATENT AND TRADEMARK OFFICE
CERTIFICATE OF CORRECTION

PATENT NO. : 6,343,502 B1
DATED : February 5, 2002
INVENTOR(S) : Ghatu Subhash, Abhijit Chandra and Brian J. Koeppel It is certified that error appears in the above-identified patent and that said Letters Patent is hereby corrected as shown below:

<u>Title page,</u>
Item [73], Assignee, delete "Michigan Technological University and insert
-- Board of Control of Michigan Technological University --.

Signed and Sealed this

First Day of April, 2003

JAMES E. ROGAN
*Director of the United States Patent and Trademark Office*